United States Patent [19]

Schultz et al.

[11] Patent Number: 5,356,439
[45] Date of Patent: Oct. 18, 1994

[54] NON-OXIDATIVE PERMANENT DYE FORMULATION FOR HAIR AND SYNTHETIC FIBERS

[75] Inventors: Thomas M. Schultz, Ridgefield; Stephanie Wong, Bridgeport, both of Conn.

[73] Assignee: Shiseido Co., Ltd., Tokyo, Japan

[21] Appl. No.: 944,407

[22] Filed: Sep. 14, 1992

[51] Int. Cl.$^5$ .............................................. A61K 7/13
[52] U.S. Cl. .......................................... 8/432; 8/405; 8/916; 8/920; 132/208; 132/202; 424/70
[58] Field of Search ............... 8/405, 406, 407, 408, 8/409, 432, 916, 920; 132/201, 208, 202, 203, 206, 210, 211; 252/301.16, DIG. 13; 424/70

[56] References Cited

U.S. PATENT DOCUMENTS

| | | | |
|---|---|---|---|
| 2,776,668 | 1/1957 | Morgan | 8/432 |
| 3,396,736 | 8/1968 | Shansky | 8/428 |
| 3,399,682 | 9/1968 | Isaii | 8/432 |
| 3,567,355 | 3/1971 | Boosen et al. | 8/432 |
| 3,912,808 | 10/1975 | Sokol | 8/405 |
| 4,781,724 | 11/1988 | Wajaroff et al. | 8/432 |
| 4,834,768 | 5/1989 | Grollier | 8/405 |
| 4,863,482 | 9/1989 | Junino et al. | 8/406 |
| 4,904,275 | 2/1990 | Grollier | 8/406 |
| 5,094,662 | 3/1992 | Schultz et al. | 8/405 |
| 5,100,658 | 3/1992 | Bolich, Jr. et al. | 8/405 |
| 5,126,126 | 6/1992 | Varaprath et al. | 252/DIG. 13 |

*Primary Examiner*—Paul Lieberman
*Assistant Examiner*—Caroline L. Dusheck
*Attorney, Agent, or Firm*—Melvin I. Stoltz

[57] ABSTRACT

By intermixing a gelling agent, water, a mercaptan-based reducing agent, and a certified dye designated as an F,D&C dye and/or a D&C dye, a highly effective, easily employed permanent dye/gel composition is obtained which imparts a desired color into both natural and synthetic fibers. In the preferred embodiment, the mercaptan-based reducing agent is added to the composition immediately prior to applying the permanent dye/gel composition to the fibers. By merely rubbing, or embrocating the permanent dye/gel composition into the natural or synthetic fibers, the desired color is permanently embedded into the fibers in a long-lasting durable manner. In view of the constituents employed in this permanent dye/gel composition, use as a permanent hair dye is highly effective.

15 Claims, No Drawings

NON-OXIDATIVE PERMANENT DYE FORMULATION FOR HAIR AND SYNTHETIC FIBERS

TECHNICAL FIELD

This invention relates to dye formulations for coloring hair and synthetic fibers and, more particularly, to dye formulations which are permanently affixed to the fibers without requiring activation by or exposure to oxidizing solutions.

BACKGROUND ART

Throughout the years, there has been a desire to alter the color of synthetic and natural fibers. In particular, coloring of human hair has been sought in view of changing styles and fashion. However, due to the inherent composition of hair fiber, and the chemical and mechanical exposure encountered by the hair fibers during normal care and styling, obtaining and maintaining a precise color has been an illusive goal.

As is well known, hair is composed of a unique protein material called "keratin" which is repeatedly being subjected to both chemical and mechanical damage from combing and brushing, as well as from sunlight, chlorinated water, shampooing, permanent waving and other such treatments involving various chemicals. As a result, depending upon the length of the hair fiber, the distal ends of each hair fiber tend to have substantially more damage than the proximal ends nearer to the scalp. This inconsistency causes variation in the dye uptake by the hair fiber, resulting in color variations along the length of the hair fiber.

In spite of the long history with the coloration of hair and the extensive effort that has been expended in attempting to eliminate the problems associated with the dyeing of human hair, no system has been achieved which is capable of overcoming all of the drawbacks and difficulties encountered with hair dyes. Included among these drawbacks is the need for a dye system which avoids any adverse effect on the skin or hair of the user.

Other problems which continue to plague conventional prior art dyes are the longevity or wearability of the resulting color, its ability to resist fading, and its ability to resist changes due to washing, combing, or rubbing. Furthermore, the accuracy of the color imparted to the hair fiber during the dyeing process, as well as the ease with which the hair fiber is capable of being dyed, are also important factors which prior art dye compositions have been incapable of successfully overcoming.

In general, prior art hair coloring and fiber coloring mixtures comprise dyestuffs obtained from coal tar derivatives or from synthetic routes. These mixtures are typically formulated to provide a particularly desired wearability of the color on the fiber. Dyes formulated for coloring hair fibers, are typically termed temporary, semi-permanent, or permanent.

Temporary dyes or hair colors last through a few shampooings, while semi-permanent hair colors are retained for three to six weeks of shampooings. The permanent dyes or colors, which are often equally employable on plant derived and synthetic fibers, as well as hair keratin, cannot be shampooed out from the fibers.

It is well known that many standard colors employed on hair or on synthetic fibers cause irritation due to the sensitivity of many individuals to these dyes. As a result, in the case of human application where hair is being dyed, a pre-application is required. In this pre-application, a small amount of color mixture is applied to the skin of the individual and allowed to remain thereon for a period of twenty-four hours, prior to use, in order to assure than an adverse reaction will not occur. If an adverse reaction is found, the dye formulation cannot be used.

It has also been found that repeated contact of the human skin to many prior art dye formulations derived from coal tars and synthetic routes often results in discomfort to the individual receiving the dye application. In addition, various other disadvantages are often encountered with the use and application of standard hair dyes and their application procedures.

Non-permanent dye formulations are principally employed in the coloring of human hair. Furthermore, most compositions used for temporarily tinting hair fibers contain acid dyes.

The nature of these non-permanent dyestuffs is to coat the fiber where the dyestuff remains on the surface of the fiber, due principally through weak electrostatic interaction. As a result, any mild mechanical stress, such as is caused by rubbing or combing the hair, causes much of the dyestuff to be removed. Furthermore, shampooing or immersion of the hair into water for any protracted time period results in a complete removal of the dyestuff and, hence, the temporary nature of the resulting color.

Semi-permanent hair coloring compositions typically comprise mixtures of one or several dyestuffs in a solution containing alcohol and water. Often the hair coloring is employed in a foam base which allows the product to be applied in various "shampoo-in" applications.

The amount of color deposited on the hair by such applications is subject to substantial variations, although the actual color deposited is typically low. In addition, grey hair is the most difficult to color in this way and loses the applied color most rapidly upon shampooing. As a result, repeated reapplications are necessary.

If an individual does not regularly have the color reapplied, the hair fibers will develop an uneven hair color, due to an uneven distribution of the dye along the hair fibers. This produces an unnatural appearance and cast to the hair. Furthermore, the repeated use required by such product causes the excess dyestuff rinsed from the hair to enter the waterways, thereby adding to the cumulative problems presently being realized in the contamination of ground water.

In view of the difficulties and drawbacks detailed above in regard to semi-permanent hair colors and temporary hair colors, individuals wishing to dye their hair have sought the use of permanent dye formulations. In particular, professional hair stylists prefer the use of permanent dye formulations, since they wish to provide their customers with more durable and longer lasting results.

In using virtually all prior art permanent hair dyes, hydrogen peroxide is required along with the particular dyestuffs. During the application, the mixture enters into the hair fibers and reacts therein to form larger dyes of a predetermined color. Since the dye molecules formed are larger than the molecules entering the hair fibers, the formed dyes are trapped within the hair fibers, and are unable to diffuse out of the fibers. Consequently, the resulting coloring is trapped within the hair fiber and is permanent.

One advantage that has been found from using these types of dye mixtures is the ability to lighten hair, since the presence of both hydrogen peroxide and the alkaline environment of the mixture will also remove natural hair color, which is then replaced by the colors formed in situ. Unfortunately, many of the dye precursors used in the formation of permanent hair colors are known to be sensitive to many individuals and, in some cases, have been purported to be active in biological systems in causing interference with different aspects of cellular action.

In the coloring of other fibrous materials, such as cotton, polyesters, nylons, non-woven fibers and fiber blends, including ramie, as found in synthetic furs, drastic chemical processes are typically required when employing coloring agents in order to achieve a durable coloring of the fibers. In some cases, it is common to use a mixture of the dyestuff with a metal salt, such as manganese, copper or cadmium water soluble complexes of a halogen, with the entire mixture being heated to high temperatures in order to use the steam in fixing the dyestuffs permanently to the fibers. In employing processes of this nature in order to dye these fibers, particular caution must be exercised since the fibers can be completely destroyed and hazardous waste material resulting from the dye process are produced, which must be carefully handled and not improperly disposed.

As is apparent from the preceding discussion, numerous attempts and extensive effort that has been expended through the long history of dye use to achieve a commercially successful dye product. However, no such product has been attained which is capable of providing a universally applicable, commercially acceptable product which overcomes all of the known drawbacks. In addition, the prior art dye systems have often proven to be expensive, which providing only limited or partial success.

Therefore, it is a principal object of the present invention to provide a permanent dye composition for use on human hair and synthetic fibers which is non-toxic and capable of being easily and successfully employed on all desired fibers with consistent, repeatable and predictable coloration results.

Another object of the present invention is to provide a permanent dye composition having the characteristic features described above which substantially reduces and virtually eliminates any irritation that may result on skin surfaces.

Another object of the present invention is to provide a permanent dye composition having the characteristic features described above which is long lasting, durable and incapable of being washed from the fibers.

Other and more specific objects will in part be obvious and will in part appear hereinafter.

DISCLOSURE OF THE INVENTION

The present invention overcomes all of the prior art drawbacks and limitations and attains a composition capable of providing permanent dyeing of hair or other fiber material in an efficient manner. These long-sought, desirable results are attained by providing a dye formulation wherein the coloring material is selected only from certified dyes, designated as either an F,D&C dye or a D&C dye. In addition, the certified coloring material is employed in a thickened solution within which is contained a mercaptan reducing agent.

In Table I, the preferred overall formulation for the permanent dye/gel composition of the present invention is provided. By employing the ingredients detailed in Table I, in the ranges identified therein, a highly effective permanent dye/gel formulation is obtained which imparts the desired color into the fibers in a permanent, long lasting, durable manner.

TABLE I

| Ingredients | Range (% by Wgt) |
| --- | --- |
| F, D & C and/or D & C Dyes | .001–5.0 |
| Gelling Agent | .01–8.0 |
| Viscosity Modulator | .001–4.0 |
| Preservative | .01–2.0 |
| Deionized Water | .99–67.0 |
| Mercaptan Reducing Agent | .01–25 |

In order to assure universal applicability of the formulations of this invention, only certified dyes approved for use by the Food and Drug Administration are employed. As a result, the only dyes incorporated into the dye formulations of this invention must be designated as either F,D&C colors or D&C colors. Dyestuff bearing the F,D&C designation have been found to be suitable for foods, drugs and cosmetics, while dyestuffs bearing a D&C designation are suitable for drugs and cosmetics. By specifically limiting the dyestuffs employed to this class of dyes, the dye formulations of this invention are incapable of causing any adverse reactions or sensitivity problems.

In Table II, representative dyes employed in the present invention are presented and identified by their F,D&C name or their D&C name, and the color index number assigned to the dye. However, these particular dyes are presented as representative of the wide variety of dyes that can be employed in the present invention, without departing from the scope of this invention.

As is evident from a review of the dyes listed in Table II, the dyes preferably employed in the dye/gel composition comprises one or more selected from the group consisting of monoazo dyes, xanthene dyes, fluorine dyes, anthraquinone dyes, and triphenylmethane dyes. However, as previously stated, any dye employed in the present invention must comprise an FDA approved dye.

TABLE II

| Certified Dyestuffs | |
| --- | --- |
| Name | Cl NO. |
| F, D & C RED #40 | Cl #16035 |
| F, D & C RED #4 | Cl #14700 |
| F, D & C BLUE #1 | Cl #42090 |
| D & C RED #22 | Cl #45380 |
| D & C RED #21 | Cl #45380A |
| D & C RED #28 | Cl #45410 |
| D & C RED #33 | Cl #17200 |
| D & C GREEN #5 | Cl #61570 |
| D & C YELLOW #8 | Cl #45350 |
| D & C YELLOW #7 | Cl #45350 |
| D & C ORANGE #5 | Cl #45370:1 |
| D & C ORANGE #4 | Cl #15510 |
| EXTERNAL D & C VIOLET #2 | Cl #60730 |

In the preferred formulation, the dye composition comprises a viscosity ranging between about 1,000 and 20,000 centipoise. It has been found that desired viscosity level is easily controlled by varying the ratos of the gelling agent and the viscosity modulator.

Although any one of a plurality of gelling agents can be employed, the preferred gelling agent is selected from guar or other cellulosic based compositions. One such gelling agent that has been found to be particularly useful in forming compositions in accordance with this invention is xanthan gum. In addition, the preferred xanthum gum is Kelgum which is manufactured by Kelco, Division of Merck & Co. of San Diego, Calif.

In addition to the gelling agent, a viscosity modulator is also employed in controlling the final viscosity of the dye formulation of this invention. Although various compositions can be employed as the viscosity modulator, the use of ammonium chloride is preferred.

As detailed in Table I, the preferred dye formulation also incorporates a preservative for enhancing the shelf life of the composition. Although any desired preservative could be employed, Merguard 1200, manufactured by Calgon Corporation Division of Merck, Inc. of Rahway, N.J. is preferred.

The final ingredient employed in the permanent dye/gel composition of this invention is a mercaptan based reducing agent. The inclusion of a mercaptan in a dye composition of the nature detailed herein is particularly unique and represents a substantial departure from the prior art teachings. Although virtually any mercaptan based agent may be employed, the preferred mercaptan based agent comprises one selected from the group consisting of esters of thioglycolic acid and esters of thiolactic acid.

In the preferred embodiment, it has been found that the mercaptan comprises one selected from the group consisting of glyceryl monothioglycolate, glyceryl monothiolactate, propylene monothioglycolate and propylene monothiolactate. In addition, as is more fully detailed below, the mercaptan based reducing agent is added to the dye/gel formulation immediately prior to the application of the dye/gel formulation to the hair or fibers.

Although the incorporation of a mercaptan based reducing agent into the permanent dye/gel formulation of the present invention is required, the quantity of the mercaptan based reducing agent employed in the final composition can be greatly varied. However, in order to attain an effective permanent dye/gel composition, it has been found that the mercaptan based reducing agent should comprise at least 0.05% by weight as a percentage of the quantity of the dyestuff incorporated into the formulation.

By employing the present invention, it has been discovered that permanent dyeing of fibers is easily attained, without requiring the application of an oxidant or activator, as is typically required with prior art permanent coloring agents. In the present invention, the dye formulation is merely applied, rubbed or embrocated into the hair to be dyed, or the fibers to be dyed, and allowed to stand for several minutes. Alternatively, if desired, the fibers may be processed under a dryer providing an output temperature ranging between about 30° C. and 70° C. Thereafter, the dye formulation is simply rinsed from the hair or fibers, leaving the hair or fibers with the precisely desired permanent coloring embedded therein.

Another unique characteristic of the present invention is the attainment of a permanent dye/gel composition which operates at a pH ranging between about 3 and 7. This is particularly unique, since prior art dye formulations operate at substantially higher pH levels.

The invention accordingly comprises a composition possessing the features, proportions, and the relation of constituents, as well as the several steps and the relation of one or more of such steps with respect to each of the other, all as fully detailed herein, with the scope of the invention being indicated in the claims.

BEST MODE FOR CARRYING OUT THE INVENTION

In order to demonstrate the unique capabilities of the present invention and prove the efficacy of the dye formulations detailed herein, the following examples are provided. In addition to providing this support, these examples are intended as a teaching of the best mode for carrying out the present invention. However, they are not intended to limit, in any manner, the breadth of this discovery.

In Table III, representative compositions of the permanent dye/gel formulations of the present invention are disclosed. In these formulations, varying amounts of the mercaptan are employed and different viscosity levels are provided. By varying the amount of the gelling agent and the viscosity modulator employed in the composition, the viscosity of the composition can be controlled between 2,000 and 6,000 centipoise. In the preferred embodiment, the viscosity is controlled by altering the ratio of xanthan gum to ammonium chloride.

TABLE III

| Ingredients | Examples (Wgt %) | | | | |
| --- | --- | --- | --- | --- | --- |
| | 1 | 2 | 3 | 4 | 5 |
| F, D & C and/or D & C Colors | 1.00 | 1.00 | 1.00 | 1.00 | 1.00 |
| Xanthan Gum | 1.00 | 2.00 | 1.00 | 1.00 | 1.00 |
| Ammonium Chloride | 1.50 | 1.00 | 1.50 | 1.50 | 1.50 |
| Preservative | 0.07 | 0.07 | 0.07 | 0.07 | 0.07 |
| Deionized Water | 95.18 | 94.18 | 94.43 | 71.43 | 94.43 |
| GMTG (80% Active) | 1.25 | 1.25 | 2.00 | 25.00 | — |
| Thiolactate ester (80.33% Active) | — | — | — | — | 2.00 |
| Viscosity (cps) | 1900 | 4400 | 1760 | 1150 | 1650 |

In determining the viscosity levels of Examples 1–5, a Brookfield Viscometer was employed, with the spindle being rotated at 30 revolutions per minute for sixty seconds. Spindle #4 was employed for Example 2, while spindle #3 was employed for each of the other examples.

Each of the formulations detailed in Table III were prepared and independently applied to numerous tresses of human hair. In each application, the permanent dye/gel formulation was prepared and then mixed with an anhydrous mixture of the mercaptan just prior to use. The final formulation was rubbed or embrocated into the hair fibers and allowed to stand for between about five and thirty minutes. After standing, the permanent dye/gel composition was rinsed from the hair.

In each test, permanent dyeing of the hair fiber was realized with uniform tonality being obtained throughout the hair fibers. No variations in dye uptake were found regardless of the viscosity of the dye compositions, and each dye composition provided a uniform permanent coloring to the hair fibers.

It is interesting to note that the composition defined by Example 4 had a substantially identical dye uptake as the compositions defined by the other examples, even though the composition of Example 4 has the lowest viscosity. It was also noted, however, that the residual odor of the mercaptan did persist with the composition of Example 4, although this residual odor was not objectionable.

In Table IV, five additional examples are provided showing specific formulations for the permanent dye/gel composition of the present invention, with specific dyes detailed therein for imparting desired color to hair.

By employing the compositions detailed in Table IV, color ranges from blue to red to yellow to brown are all easily achieved using commercially available dyestuffs.

When applied to tresses of human hair, in the manner detailed above, these compositions were found to be highly effective in providing a long-lasting, permanent dye to the hair fibers. However, the formulations defined in Table IV are provided as examples of the scope of the present invention, and are not intended to limit the scope of this invention or the combinations or variations that can be made without departing from the scope of the present invention.

TABLE IV

| Ingredients | Examples (Wgt %) | | | | |
|---|---|---|---|---|---|
| | 6 | 7 | 8 | 9 | 10 |
| GMTG (80% Active) | 2.00 | 2.00 | 2.00 | 2.00 | 2.00 |
| Xanthan Gum | 1.00 | 1.00 | 1.00 | 1.00 | 1.00 |
| Ammonium Chloride | 1.50 | 1.50 | 1.50 | 1.50 | 1.50 |
| Preservative | 0.07 | 0.07 | 0.07 | 0.07 | 0.07 |
| Deionized Water | 75.13 | 74.93 | 74.93 | 74.63 | 74.83 |
| F, D & C Blue #1 | 0.30 | | | | |
| D & C Red #28 | | 0.50 | | | |
| D & C Red #22 | | | 0.50 | | |
| D & C Replacement Brown #1 | | | | 0.80 | |
| D & C Orange #5 | | | | | 0.60 |

One of the principal discoveries that has been found by employing the present invention is that the use of the permanent dye/gel composition detailed herein imparts a permanent coloring to the hair, or other fibers to which they are applied, by permanent attaching within the hair or fiber matrix. In addition, certified colorants employed in the permanent dye/gel formulation of this invention operate as acid compositions and provide both durable and long-lasting coloring. Although the actual mechanism by which the present invention operates is unknown, the results achieved by the present invention are easily observed, and are detailed below.

In order to provide repeatable, objective, quantitative measurements of the hair coloring achieved by the present invention, a colorimeter was employed, and the dyed hair samples were tested for color permanency, durability, washability and fading. A colorimeter was employed, since it measures the intensity of the lightness, hues and tones of the hair, as delineated in the C.I.E. Scale for color measurements. In these measurements, the chromaticity values of L, a, and b are employed, wherein L equals the total reflectance of the hair fiber, with black equal to a value of 0 and white equal to a value of 100, while a equals a positive value for red and a negative value for green and b equals a positive value for yellow and a negative value for blue. For consistency, all measurements were taken employing a Spectroguard 2 system available from Pacific Instruments.

In order to further quantify the measurements taken, the following equation was employed, which defines the overall loss of color as $\Delta E$:

$$\Delta E = \sqrt{(L_f - L_i)^2 + (a_f - a_i)^2 + (b_f - b_i)^2}$$

where i=initial value and f=final measurement.

EXAMPLE 11

Tresses of human hair having a brown level 6 color were dyed employing the permanent dye/gel composition detailed in Example 7, using the procedure detailed above. The resulting dyed hair acquired a deep auburn color.

After the tresses were allowed to dry for twenty-four hours at ambient temperatures and relative humidity, the tresses were covered throughout with a mixture of 12% hydrogen peroxide and 3%–5% persulfate. After an exposure time of thirty minutes to this solution, the tresses were rinsed and dried. Observations of the dry tresses showed that all of the natural underlying pigment of the hair had been lost. However, the bright red color of the dye remained, completely impervious to the oxidation system. This clearly proved that the permanent dye/gel composition of this invention produces a permanent and stable coloring to the hair, which is completely unaffected by subsequent oxidation. The test results obtained are detailed in Table V.

TABLE V

| | Wearability by Action of Bleach | |
|---|---|---|
| | Prior to Exposure | After Bleached |
| L = | 18.74 | 35.11 |
| a = | 5.09 | 30.00 |
| b = | 0.19 | 16.32 |
| $\Delta E$ = | | 33.89 |

EXAMPLES 12–15

In order to prove the wearability and durability of the coloring resulting from the use of the permanent dye/gel formulations of the present invention, several tresses of human hair having a level 5 brown color were dyed in accordance with the present invention, employing each of the dye/gel formulations defined in Table IV. The resulting dyed tresses provided variously accented brown hair.

Each of the tresses were then subjected to 12 cycles of shampooing, rinsing, and drying, with the chromaticity values determined both before and after the exposure to the 12 cycles. The resulting values are provided in Table VI, wherein the overall color loss shown by each of the different formulations is provided. As is evident from these results, a minimum color loss was experienced, thereby proving the durability of the dye formulations of this invention.

As part of the same test procedure, other hair tresses, which were dyed in the identical manner, were exposed to artificial sunlight, obtained by employing a carbon-arc lamp, for a period of ten continuous hours. The instrument used for this operation was the Atlas Fade-O-Meter, Model #22-A. The chromaticity values obtained both before and after the exposure to the light source are provided in Table VI along with the resulting $\Delta E$ or color loss measurement. As is apparent from the data provided in Table VI, only a minimal color loss occurred, showing the unusual and unexpected stability of the hair fibers dyed in accordance with this invention to light exposure. Typically, F,D&C dyestuffs would be expected to incur substantial fading under these conditions. However, by employing the formulations of the present invention, a completely unexpected, stable, non-fading color was obtained in each of the samples.

TABLE VI

| | Wearability to Shampoo and Sunlight | | | |
|---|---|---|---|---|
| Dye/Gel Formulation | | Initial | Shampoo (12x cycle) | Initial | Weatherometer (ten hours) |
| Example 6 | L = | 28.05 | 28.72 | 25.79 | 26.95 |
| | a = | 5.34 | 5.51 | 4.41 | 4.01 |

TABLE VI-continued

Wearability to Shampoo and Sunlight

| Dye/Gel Formulation | | Initial | Shampoo (12x cycle) | Initial | Weatherometer (ten hours) |
|---|---|---|---|---|---|
| | b = | 8.28 | 10.20 | 6.86 | 6.96 |
| | ΔE = | | 2.04 | | 1.23 |
| Example 7 | L = | 18.25 | 19.65 | 19.95 | 2.09 |
| | a = | 3.93 | 3.42 | 3.99 | 3.81 |
| | b = | 0.51 | 0.56 | 0.16 | 1.17 |
| | ΔE = | | 1.49 | | 1.04 |
| Example 8 | L = | 26.96 | 28.89 | 26.96 | 26.98 |
| | a = | 3.12 | 3.68 | 3.12 | 3.25 |
| | b = | 5.88 | 7.85 | 5.88 | 6.35 |
| | ΔE = | | 2.81 | | 0.49 |
| Example 9 | L = | 19.90 | 20.09 | 19.95 | 19.93 |
| | a = | 3.68 | 3.14 | 3.99 | 3.71 |
| | b = | 0.42 | 0.31 | 0.16 | 0.32 |
| | ΔE = | | 0.58 | | 0.32 |

EXAMPLES 16 and 17

Another difficulty typically encountered from the use of prior art dye compositions is the inability of the dyed hair to be treated with standard permanent wave lotions. Typically, dyed hair undergoes substantial loss of the imparted color when the dyed hair is exposed to mercaptan-based permanent waving formulations. However, when the permanent dye/gel compositions of the present invention are employed, exposure of the dyed hair to permanent wave lotions failed to cause any loss degradation of the imparted color.

In Table VII, the test results obtained are provided. In conducting these tests, tresses of human hair having a brown, level 6 color were dyed employing the composition detailed in Example 7 of Table IV and the method defined above. The dyed tresses were allowed to dry for twenty-four hours at ambient temperature and humidity, and then the tresses were permanently waved using either an acid-based permanent wave or an alkaline-based permanent wave.

Chromaticity values were taken on the hair tresses both before and after the permanent wave applications, and these values are detailed in Table VII.

TABLE VII

| | Initial | After Permed |
|---|---|---|
| Alkaline | | |
| L = | 18.15 | 21.28 |
| a = | 4.94 | 4.83 |
| b = | 0.03 | 0.87 |
| ΔE = | | 3.24 |
| Acid | | |
| L = | 18.25 | 20.64 |
| a = | 3.93 | 4.63 |
| b = | 0.51 | 0.41 |
| ΔE = | | 2.49 |

Although any conventional acid or alkaline based permanent wave lotion could have been employed, the acid-based permanent wave employed for this test was ACCLAIM, sold by Zotos International, Inc. of Darien, Conn. and the alkaline-based permanent wave employed was DESIGN FREEDOM, sold by Zotos International, Inc. of Darien, Conn.

EXAMPLE 18

Another difficulty typically encountered with dyed hair is the inability to redye the hair and maintain the same color or shade. Typically, prior art dyes fade or become "weathered", which causes any subsequent dye application to impart a different shade or tint to the hair.

With the present invention, it has been found that dyed hair can be repeatedly redyed, with an additive effect being obtained. With the present invention, the colors become richer, with the same shade and tone consistently added to the hair.

In Table VIII, the test results obtained are provided. In conducting these tests, tresses of virgin human hair having a level 1 dark brown color were dyed using the procedures detailed above. Then, the tresses were redyed two additional times, using the same procedures. The chromaticity values obtained after each dye cycle are provided in Table VIII, along with the overall color change (ΔE). As is apparent from the results provided in Table VIII, variations in color did not occur upon redyeing and, instead, substantially consistent results were obtained after each redyeing application.

TABLE VIII

| | Redyed Hair | | |
|---|---|---|---|
| | Initial Dyed | 2nd Redyed | 3rd Redyed |
| L = | 19.81 | 19.60 | 18.51 |
| a = | 5.71 | 6.54 | 6.58 |
| b = | 1.58 | 1.62 | 5.27 |
| ΔE = | | | 4.03 |

EXAMPLES 19–20

In addition to its effectiveness on human hair fibers, the permanent dye/gel formulations of the present invention have also been found to be equally effective when applied to synthetic fibers, such as fur and textiles. In order to prove the efficacy of the invention when applied to such compositions, the dye formulation detailed in Example 7 was applied to a synthetic brown/white fur formed from a nylon and polyester blend.

After the initial dye application, the fur was subjected to twelve cycles of shampoo, rinse and drying, in order to establish the durability of the dye. The chromaticity values obtained after the initial dye application, as well as after the twelve repeated shampoo cycles, are provided in Table IX.

The resulting data showed virtually no color change from the exposure to twelve shampoo/rinse/dry cycles. As is clearly apparent from these results, the permanent dye/gel formulations of the present invention are permanently embedded into the fur fibers, in a manner which prevents any overall color loss to be experienced by the fur even after twelve shampoo, rinse and dry cycles.

TABLE IX

| Dye Durability on Fur and Carpet Fibers | | |
|---|---|---|
| | Initial | After Shampoo Cycles |
| Rabbit Fur | | |
| L = | 45.35 | 44.24 |
| a = | 65.66 | 68.36 |
| b = | −3.11 | −3.85 |
| ΔE = | | 3.01 |
| Carpet | | |
| L = | 55.05 | 65.20 |
| a = | 61.64 | 57.76 |
| b = | 0.21 | 3.29 |
| ΔE = | | 11.29 |

In addition, a synthetic carpet, having an off-white color and formed from nylon fibers, was dyed using the same dye formulation and procedure detailed above.

The dyed carpet was then subjected to twelve repeated cycles consisting of shampoo, rinse and dry, with the chromaticity value being determined after completion of the twelfth cycle. The test results obtained both initially and after the twelfth cycle are detailed in Table IX.

As is apparent from the results obtained from the dyed synthetic carpet, the dye formulation was able to impart a permanent color to the synthetic fibers which completely resisted being washed out by repeated shampoo, rinse, and dry cycles. Clearly, as detailed herein, the permanent dye/gel formulations of the present invention are capable of providing a long lasting, durable, permanent coloring to hair fibers, and to synthetic fibers.

It will thus be seen that the objects set forth above, among those made apparent from the preceding description, are efficiently attained and, since certain changes may be made in the composition detailed herein, as well as in carrying out the above process, without departing from the scope of the present invention, it is intended that all matter contained in the above description shall be interpreted as illustrative and not in a limiting sense.

It is also to be understood that the following claims are intended to cover all of the generic and specific features of the invention herein described and all statements of the scope of the invention in which, as a matter of language, might be said to fall therebetween.

Particularly, it is to be understood that in said claims, ingredients or compounds recited in the singular are intended to include compatible mixtures of such ingredients wherever the sense permits.

Having described our invention, what we claim as new and desire to secure by Letters Patent is:

1. A highly effective, easily employed permanent dye and gel composition for use on natural and synthetic fibers free from oxidants and activators for imparting a desired color into the fiber in a permanent and long-lasting manner employing a single, one-step application, said composition comprising
   A. between about 0.001% and 5.0% by weight of at least one dyestuff selected from the group consisting of certified dyes designated as F,D&C dyes and D&C dyes;
   B. viscosity controlling additives for maintaining the viscosity of said composition to between about 1,000 and 20,000 centipoise and comprising
      a. between about 0.01% and 8.0% by weight of a gelling agent comprising one selected from the group consisting of guar and cellulosic based compositions; and
      b. between about 0.01% and 4.0% by weight of ammonium chloride;
   C. between about 0.01% and 25% by weight of a mercaptan-based reducing agent wherein said mercaptan-based reducing agent is further defined as comprising at least 0.5% by weight of the dyestuff; and
   D. water forming the balance with the resulting pH of the composition ranging between about 3.0 and 7:0;
whereby a permanent dye and gel composition is attained which is easily applied to the desired fiber in a single, one-step application and imparts the precisely desired color into the fiber in a permanent long-lasting durable manner.

2. The permanent dye and gel composition defined in claim 1, wherein said dyestuff is further defined as comprising at least one selected from the group consisting of monoazo dyes, xanthene dyes, fluorine dyes, anthraquinone dyes, and triphenylmethane dyes.

3. The permanent dye and gel composition defined in claim 1, wherein the viscosity of said composition comprises between about 2,000 and 6,000 centipoise.

4. The permanent dye and gel composition defined in claim 3, wherein the viscosity thereof is controlled by varying the ratio of the gelling agent to the ammonium chloride.

5. The permanent dye and gel composition defined in claim 1, wherein said gelling agent is further defined as comprising xanthan gum.

6. The permanent dye and gel composition defined in claim 1, wherein the mercaptan based reducing agent is further defined as comprising one selected from the group consisting of esters of thioglycolic acid and esters of thiolactic acid.

7. The permanent dye and gel composition defined in claim 6 wherein the mercaptan based reducing agent is further defined as comprising one selected from the group consisting of glyceryl monothioglycolate, glyceryl monothiolactate, propylene monothioglycolate and propylene monothiolactate.

8. A highly effective, easily employed permanent dye and gel composition for use on natural and synthetic fibers free from oxidants and activators for imparting a desired color into the fibers in a permanent and long-lasting, durable manner, and in a single one-step application said composition consisting essentially of
   A. between about 0.3% and 1.0% by weight of at least one certified dyestuff selected from the group consisting of dyestuffs designated as F,D&C dyes and D&C dyes;
   B. between about 1.0% and 2.0% by weight of xanthan gum;
   C. between about 1.0% and 1.50% by weight of ammonium chloride;
   D. between about 1.25% and 25% by weight of a mercaptan based reducing agent; and
   E. water forming the balance with the resulting pH of the composition ranging between about 3.0 and 7.0.

9. The permanent dye and gel composition defined in claim 8, wherein said composition further comprises a preservative.

10. The permanent dye and gel composition defined in claim 8, wherein said mercaptan based reducing agent is further defined as comprising an 80% active solution of glyceryl monothioglycolate.

11. The permanent dye and gel composition defined in claim 8, wherein the mercaptan based reducing agent is further defined as comprising an 80.33% active solution of an ester of thiolactic acid.

12. The permanent dye and gel composition defined in claim 8, wherein the certified dyestuff is further defined as comprising at least one selected from the group consisting of F,D&C Blue No. 1, D&C Red No. 28, D&C Red No. 22, and D&C Orange No. 5.

13. A single, one-step application process for permanently imparting a desired color into natural or synthetic fibers in a long-lasting durable manner comprising the steps of:
   A. mixing between about 0.001% and 5.0% by weight of a desired dyestuff into an aqueous solution wherein said dyestuff comprises a certified dyestuff selected from the group consisting of F,D&C dyes and D&C dyes;

B. adding to the mixture of step A between about 0.01% and 8% by weight of a gelling agent comprising one selected from the group consisting of guar and cellulosic based compositions;

C. intermixing therewith between about 0.01% and 4.0% by weight of ammonium chloride, with the ratio of the gelling agent and ammonium chloride being varied to control the viscosity of the final composition to between about 1,000 and 20,000 centipoise, forming a permanent dyestuff gel composition.

D. intermixing into said permanent dyestuff gel composition between about 0.01% and 25% by weight of a mercaptan based reducing agent, with said reducing agent comprising at least 0.5% by weight of the dyestuff and being added to the composition immediately prior to use of the composition on the fiber;

E. applying the fully formulated permanent dyestuff gel composition to the fibers to be dyed by rubbing or embrocating the composition into the fibers;

F. allowing the permanent dyestuff gel composition to remain on the fibers for between about 5 and 30 minutes; and G. rinsing the permanent dyestuff gel composition from the fibers, leaving the fibers with the precisely desired permanent coloring embedded therein.

14. The process defined in claim 13, comprising the additional step of:

A. applying heat to the fibers after the permanent dyestuff gel composition has been applied to the fibers with the temperature of the applied heat ranging between about 30° C. and 70° C.

15. A single, one-step application process for permanently imparting a desired color into natural or synthetic fibers in a long-lasting durable manner consisting essentially of:

A. mixing between about 0.001% and 5.0% by weight of a desired dyestuff into an aqueous solution wherein said dyestuff comprises a certified dyestuff selected from the group consisting of F,D&C dyes and D&C dyes;

B. adding to the mixture of step A between about 0.01% and 8% by weight of a gelling agent comprising one selected from the group consisting of guar and cellulosic based compositions;

C. intermixing therewith between about 0.01% and 4.0% by weight of ammonium chloride, with the ratio of the gelling agent and ammonium chloride being varied to control the viscosity of the final composition to between about 1,000 and 20,000 centipoise, forming a permanent dyestuff get composition.

D. intermixing into said permanent dyestuff gel composition between about 0.01% and 25% by weight of a mercaptan based reducing agent, with said reducing agent comprising at least 0.5% by weight of the dyestuff and being added to the composition immediately prior to use of the composition on the fiber;

E. applying the fully formulated permanent dyestuff gel composition to the fibers to be dyed by rubbing or embrocating the composition into the fibers;

F. allowing the permanent dyestuff gel composition to remain on the fibers for between about 5 and 30 minutes;

G. applying heat to the fibers after the permanent dyestuff gel composition has been applied to the fibers with the temperature of the applied heat ranging between about 30° C. and 70° C.; and H. rinsing the permanent dyestuff gel composition from the fibers, leaving the fibers with the precisely desired permanent coloring embedded therein.

* * * * *